United States Patent [19]
Kelly et al.

[11] Patent Number: 5,676,745
[45] Date of Patent: Oct. 14, 1997

[54] PRE-CERAMIC POLYMERS IN FABRICATION OF CERAMIC COMPOSITES

[75] Inventors: John Robert Kelly, Derwood; Joseph M. Antonucci, Kensington, both of Md.

[73] Assignee: The United States of America, as represented by the Secretary of Commerce, Washington, D.C.

[21] Appl. No.: 487,557

[22] Filed: Jun. 7, 1995

[51] Int. Cl.$^6$ ....................................................... C09K 3/00
[52] U.S. Cl. ........................ 106/35; 501/1; 501/32; 501/127; 501/80; 501/153; 501/154; 501/103; 501/134; 424/422; 424/423; 433/222.1; 433/201.1; 433/212.1; 428/306.2; 428/307.3; 427/376.2; 427/245; 427/2.26; 427/2.27; 427/2.29
[58] Field of Search ....................... 501/32, 1, 127, 501/12, 134, 80, 153, 103, 154; 106/35; 424/422, 423; 433/222.1, 201.1, 212.1; 523/113, 115, 116; 428/306.6, 307.3; 427/376.2, 245, 2.26, 2.27, 2.29

[56] References Cited

U.S. PATENT DOCUMENTS

| | | | |
|---|---|---|---|
| 3,662,405 | 5/1972 | Borzt et al. | 501/80 |
| 3,867,156 | 2/1975 | Fukumoto et al. | 501/12 |
| 4,222,128 | 9/1980 | Tomonaga et al. | 433/201.1 |
| 4,231,900 | 11/1980 | Kato et al. | 427/376.2 |
| 4,608,350 | 8/1986 | Howard, Jr. | 501/12 |
| 4,897,370 | 1/1990 | Horiguchi et al. | 501/12 |
| 5,358,910 | 10/1994 | Atwell et al. | 501/80 |

FOREIGN PATENT DOCUMENTS 2-161941  6/1990  Japan ................... 433/201.1

*Primary Examiner*—Melissa Bonner
*Attorney, Agent, or Firm*—Watson Cole Stevens Davis, P.L.L.C.

[57] ABSTRACT

Composites in the form of a three-dimensional framework or skeleton of ceramic particles are formed by a low cost, low temperature sintering process which decomposes a pre-ceramic inorganic or organic precursor. Upon heating, preferably in air, the precursor decomposes to form a ceramic phase in the form of necks between the individual ceramic particles. The properties of the resulting porous ceramic bodies can be modified, such as toughened by impregnation with monomers, oligomers or polymers which are polymerized or cured in situ. Such composites find use as cosmetic products or protheses for humans and animals, such as dental restoratives and bone implants. Methods of fabrication are disclosed which include the use of a pre-ceramic polymer as a binder for the ceramic particles which forms the necks of material between the individual ceramic particles upon firing.

27 Claims, 1 Drawing Sheet

PRE-CERAMIC POLYMERS IN FABRICATION OF CERAMIC COMPOSITES

BACKGROUND OF THE INVENTION

1. Field of the Invention

The invention is disclosed to a new class of composites comprising a ceramic powder which is formed into a three-dimensional network or skeleton through the use of a ceramic-forming inorganic or organic precursor which forms "necks" or bonds between the individual particles of the ceramic powder, and which, upon firing at elevated temperatures, forms a true ceramic bond between the particles. The powders may be coated on a substrate prior to firing, or may be compacted, molded, or used in conjunction with metallic preforms. After firing, the coatings, moldings, compacts and metallic-ceramic composites may be used as such or may be further impregnated with another material, e.g., a monomer which is polymerized in situ to form a new class of composite materials.

2. Description of the Related Art

It is known to cause sintering of ceramic powder particles under conditions of elevated temperature. For example, a metal oxide powder, such as alumina, will sinter by placing the ceramic powder in an environment having a temperature in excess of 1100° C. It is also known to use a binder, such as an organic resin to give the ceramic powder "green strength". However, upon firing, the binder generally turns into a vapor and is not present in the sintered ceramic.

Thus, there remains in the art the requirements of high temperature, requiring large amounts of energy to form sintered articles, which sometimes requires the use of temporary binders which serve no useful function after sintering, resulting in an extra cost in the manufacturing process which yields no beneficial effect in the sintered product.

OBJECTS OF THE INVENTION

It is an object of the invention to provide improved properties in composite materials comprising ceramic powders.

It is a further object of the invention to provide simplified, low cost, low temperature methods of fabrication of ceramic materials.

It is a still further object of the invention to provide a new class of composite materials based on incorporating organic infiltrants into at least a partially sintered ceramic skeleton or framework.

Another object of the invention is to provide new materials suitable for use as prostheses or cosmetic products, especially for dental and hard tissue replacement in animals and humans, especially dental restorations, cranial and bone plates, bone implants, replacement fingernails, composite implants such as metal-ceramic pins, screws, and other fasteners, structural products of improved toughness, low cost, low temperature coatings for enamelware, and other products based on ceramic powders.

These and other objects will be apparent to the skilled artisan from the following description of the invention.

SUMMARY OF THE INVENTION

The first step in forming the new materials of the invention lies in creating a porous ceramic body, the ceramic framework of the interpenetrating phase composite (hereinafter "IPC") having an inorganic phase, e.g., ceramic as one component, by introducing and pyrolyzing a pre-ceramic inorganic or organic precursor material.

During initial sintering "necks" of the ceramic precursor material form between individual particles of the ceramic powder, usually as the result of surface coating, and with heating under appropriate conditions, bind the individual particles together via ceramic bonds formed as interparticle necks by decomposition of the organic precursor material thus forming a framework or skeleton of a porous partially sintered body of ceramic.

In order to reduce the sintering conditions, e.g., time and/or temperature, a ceramic forming pre-ceramic forming inorganic or organic material, e.g., a monomer, oligomer or polymer can be introduced into the ceramic powder, usually in a solvent, to assist in the forming of the necks of material between the individual ceramic particles to form the ceramic particles into a porous framework.

Upon formation of the porous, three-dimensional framework or skeleton, the porous ceramic skeleton may be subsequently impregnated with a second polymeric material, which may be the same as the pre-ceramic polymer, or different, e.g., a poly(methyl methacrylate).

For example, polymerization of the organic material, e.g., methyl methacrylate, within the porous framework results in translucent blocks which are easily machined and have tensile strengths ranging from 50–200 MPa.

Alternatively, the pre-ceramic forming inorganic or organic material and ceramic powder can be coated onto a preform, such as a titanium pin or screw, or a substrate, such as enamelware, and heated to a suitable temperature to form a low cost, low temperature coating. In certain embodiments, the coating may be subsequently infiltrated by a toughening organic material, which may be the same as, or different from, the precursor forming inorganic or organic material, to introduce further specific properties, such as aesthetics, scratch-resistance, chipping resistance, hydrophobicity, dielectric properties or bioactivity.

DETAILED DESCRIPTION OF THE INVENTION

Figure 1:
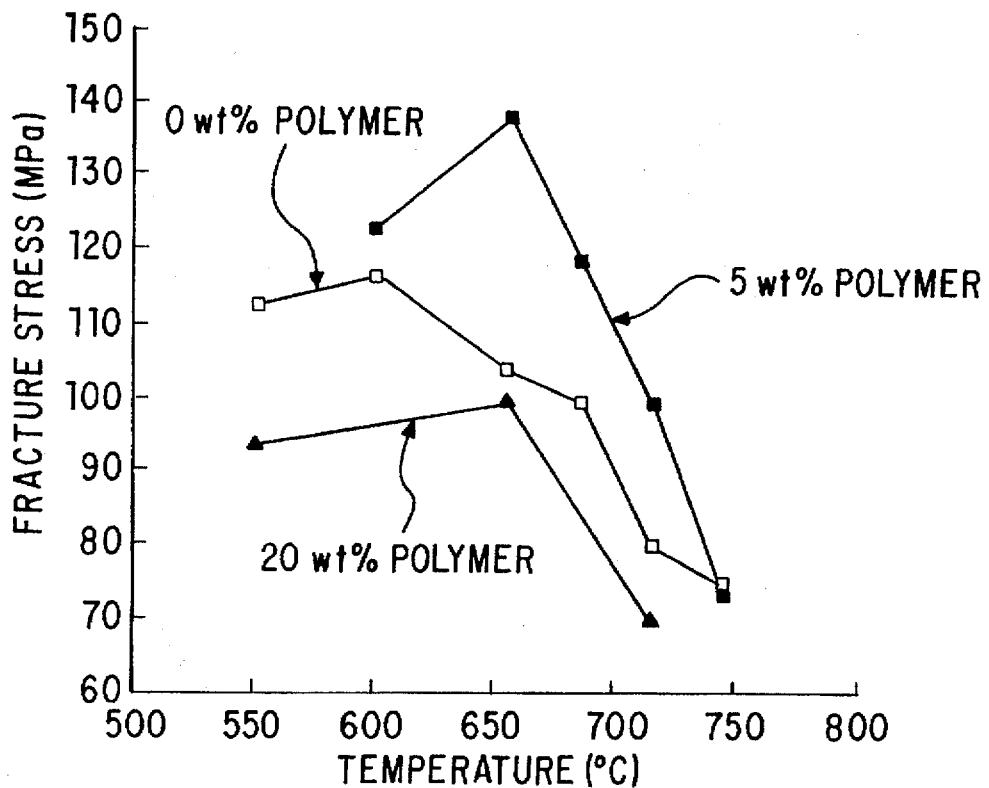
FIG. 1 is a graphic representation of the mean fracture stress as a function of pyrolysis temperature for the weight percentage of each of the poly(dimethylsiloxane) solutions depicted therein.

The first step in creating an interpenetrating phase composite (IPC) involves compacting a suitable ceramic powder. Theoretically any ceramic powder can be employed in the invention. By "ceramic" throughout the specification and claims, we mean metal oxides, such as alumina, as well as non-oxides of metal, e.g., silicon nitride and silicon carbide; in either the crystalline, or amorphous, state, e.g., glasses. Examples of suitable ceramics include alumina, zirconia, spinels, titanium dioxide, biologically active glass (such as these sold under the trademark BIOGLASS), feldspathic ceramics, such as, feldspathic dental ceramics, and calcium hydroxyapatites. Ceramics also include mixed powders including mixed glassy powders with metal oxides. Particle size is preferably in a range of particle size so as to achieve any desired packing density. While dense packing may be desirable in certain circumstances, in all cases the production of porous bodies is desirable, with the degree of porosity being varied so as to yield, with the incorporation of an inorganic or organic material infiltrant, the desired properties. Generally porosity in the resulting framework or skeleton is about 25–50% by volume, preferably 35–40% by volume.

In certain circumstances, such as in forming dental restorations, extremely fine particle size of ceramic particles on the order of 0.5 micrometer, are desirable especially to avoid excess wear on the opposing tooth. Such particles sizes are operative within the present invention.

The organic material selected from the pre-ceramic forming material is a material which forms the necks binding the individual ceramic particles under appropriate firing conditions. By appropriate firing conditions, we mean from 1 minute to 1 hour at temperatures of from about 500° C. to about 1000° C. Preferred firing conditions are about 10 minutes at about 655° C. Sintering atmospheres should not degrade either the ceramic powder or the function of the pre-ceramic forming organic material. Thus, inert atmospheres are acceptable, though not critical. Sintering in air is preferable. In certain circumstances, reactive atmospheres, such as nitrogen, can be employed. Both temperatures and pressure can be varied to control the nature of the resulting porous framework.

A suitable glass-forming pre-ceramic inorganic or organic material is a polymer of poly(dimethylsiloxane). Most preferably, we employ a poly(dimethylsiloxane) having a kinematic viscosity of about 1000 centistokes which polymer is trimethylsiloxy terminated. Such a polymer forms a high-silica content glass at moderate temperatures in air. The polymer can suitably be mixed with the ceramic powder by use of a solvent. Content of the pre-ceramic organic material can vary between about 2.5%. by weight, to about 20% by weight, although greater or lesser amounts of polymer can be employed. We have employed five percent (by weight) of poly(dimethylsiloxane) in a solvent such as cyclohexane.

Preferred suitable inorganic and organic materials include polyorganozirconates, polyorganoaluminates, polysiloxanes, polysilanes, polysilazanes, polycarbosilanes, polyborosilanes, etc. Suitable pre-ceramic forming materials are currently commercially available from Gelest, Inc. of Tullytown, Pa., such as zirconium tetramethacrylate, zirconyl dimethacrylate, or zirconium 2-ethylhexanoate; aluminum III s-butoxide, aluminum III diisopropoxide-ethylacetoacetate; 1,3-bis(chloromethyl) 1,1,3,3-Tetrakis (trimethylsiloxy)disiloxane; 1,3-bis(3-carboxypropyl) tetramethyldisiloxane; 1,3,5,7-tetraethyl-2,4,6,8-tetramethylcyclotetrasilazane; tris(trimethylsilyl)phosphate; and tris(trimethylsiloxy)boron. Average molecular weight of the organic precursor materials varies between about 150 to about 200,000.

In addition to the various inorganic and organic materials discussed above, other precursor polymers suitable for use in the invention include polyphosphazenes, polyorganotitanates and other organometallic polymers. Monomeric and oligomeric forms of the various polymeric materials mentioned as infiltrants also may be used to infiltrate the porous ceramic framework or skeleton. Additionally, various combinations of the above polymers, polymer/monomer, and monomer/monomer mixtures can be used as the infiltrant.

In addition to the infiltrants mentioned above, which can also be used as the ceramic-forming precursor, it is within the scope of the present invention to use infiltrants other than the pre-ceramic precursor materials to form a second phase within the porous framework.

The infiltrants may perform multiple functions, such as toughening the skeleton or framework, such as in providing "active" sites to aid in bonding the infiltrated composite (IPC), via an adhesive or cement, to a substrate through chemical bonding. In the past, prostheses, such as dental restorations, formed from a ceramic, were typically bonded, via an intervening adhesive or cement, to a substrate exclusively through mechanical interlocks. Such mechanical interlocks were formed by abrading or etching the prosthesis to form mechanical sites into which the adhesive or cement could penetrate and interlock. While such mechanical sites may still be provided on the composites of the present invention, the infiltrant can also be a source for chemical (in addition to the mechanical) bonding. Reactive functionality in the infiltrant can be preserved even after the polymerization of the infiltrant within the skeleton or framework, which functionality assists in the formation of chemical bonds to the adhesive or cement.

Thus, the present invention has utility for forming dental restorations, including crowns or partial dentures, onlays and inlays. The restorations may be molded in conventional gypsum dental molds. Alternatively, restorations may be formed from a mixture of ceramic particles, pre-ceramic precursor and a light, e.g., ultraviolet (UV) or visible light, curable resin to sustain formed shapes and impart workability for the technician. Still further, the composites of the present invention may be made into blocks of restorative material and machined to the final shape.

Such machining processes include computer assisted design/computer assisted machining (CAD/CAM) which utilize very simple block shapes of restorative material, removing many of the traditional processing restrictions which limited material choices for restorative dentistry.

Other uses of the composite materials of the claimed invention are as a coating for implants, e.g., coatings on titanium pins or screws. In corrective surgery, there is usually a requirement to remove a pin or screw necessitating a second surgery. The space around the screw does not reliably fill with new bone growth. By forming a ceramic coating, such as calcium hydroxyapatites and pre-ceramic precursor according to the invention, the coating will bind the porous skeleton firmly to the surgical implants, such as onto metal pins or screws. The porous nature of the composite facilitates bone growth into the hydroxyapatites framework.

The nature of the composite material also permits its use as a directly implantable body, i.e., a cranial or bone plate or bone implant, where the porosity of the framework facilitates bone growth within the framework.

Even where the framework is infiltrated to modify the properties (e.g., toughen) of the framework, the infiltrant can be partially etched or leached from the framework to expose the porous structure to facilitate bone growth. Alternatively, the framework can be selectively impregnated to different degrees by the infiltrant or impregnated with a bioresorbable material.

The present invention provides low cost, low temperature benefits which may be utilized outside of prosthetics, such as commercially as chip resistant coatings for enamelware, whiteware fabrication and tile fabrication.

The fabrication of IPC blocks according to the invention will now be described in detail in the following Examples.

Example 1

Starting blocks of ceramic framework were formed as follows:

A feldspathic ceramic (sold under the tradename Ceramico II, from Johnson & Johnson, Inc.) was mixed with solutions of various weights of poly(dimethylsiloxane), trimethylsiloxy terminated, 1000 CS, in cyclohexane, and shaped into discs by pressing in a 12.6 mm die at 428 megapascals for 30 seconds.

The discs were fired for 10 minutes at temperatures ranging from 550°–745° C. The resulting discs were porous and were silanated with 3-methacryloxypropyltrimethoxysilane and then infiltrated with methyl methacrylate activated with a chemical initiator system (2 wt % benzoyl peroxide and 0.5 wt % N,N-dihydroethyl-p-toluidine).

After 24 hours ambient (22° C.) polymerization, the excess polymer was removed and the resulting easily machinable discs were tensile tested in biaxial flexure. Initially a 2×3 factorial design with n=3–8 per group was used to assess the effects of the two factors, temperature (for 10 minutes) at two levels: low temperature (655° C.) and high temperature (715° C.) and binder concentration at three levels: 0 wt %, 5 wt % and 20 wt %. Temperature and binder concentration were both significant (p<0.001). The interaction between temperature and concentration was not significant (p>0.76). Duncan's Multiple Comparison (alpha=0.1) test was used to determine specific differences among the three concentrations. Significant differences were found between 0 and 5 wt % and between 5 and 20 wt %.

Example 2

Based on the results of Example 1, the 5 wt % binder was studied at temperatures of 550° C., 600° C., 655° C., 685° C., 715° C. and 745° C. As a result, it was found that optimum temperature for the 5 wt % binder appears to be about 655° C. yielding an IPC with a mean tensile strength of 140 MPa. The ceramic powder used in this example was a leucite containing feldspathic dental porcelain used for metal-ceramic dental restorations (Ceramics II, incisal light. Johnson & Johnson, Inc.). The poly(dimethylsiloxane) was trimethylsiloxy terminated and had a viscosity of 0.001 $m^2/sec$ (Petrauch Systems, Bristol, Pa.). Cyclohexane was used as a solvent, or carrier, for the siloxane.

Individual test specimens were prepared from 0.5 grams of feldspathic porcelain and 14 drops (approx. 0.7 ml) of the siloxane solution. Concentrations of pre-ceramic polymer were evaluated for 0%, 5% or 20% by weight. Powder specimens were pressed as in Example 1. Pressed powder discs were then fired in air for 10 minutes at one of six temperatures mentioned above ranging from 550° C. to 745° C.

The porous, pressed discs were silane treated with a common coupling agent. 3-methacryloxy-propyltrimethoxy silane. Silanation was used both to prepare the interparticle-necked ceramic mixture for monomer infiltration as well as to maximize later physical properties.

Following silanation, specimens were infiltrated as in Example 1. A 24 hour ambient temperature cure was followed by a 65° C. post-cure or annealing.

Excess polymer was removed from the discs using rotary instruments and abrasive paper. Specimens were finished only through 600 grit, and were therefore not highly polished. Discs were tested using biaxial flexure in a pin on 3 ball fixture at a crosshead speed of 0.5 mm/min. Failure stresses were calculated using the equation of Wachman (*J. Mater. Sc.*, 7:188–194, 1972; herein incorporated by reference).

As can be seen from Table 1 below, the experimental matrix consisted of 72 specimens distributed over three different pre-ceramic polymer concentrations and six temperatures, ranging from 550° C. to 745° C. It can be seen that the specimens were not uniformly distributed over the matrix.

TABLE 1

| Pyrolysis Temperature | 0 wt % | 5 wt % | 20 wt % |
| --- | --- | --- | --- |
| 550 | 2 | — | 2 |
| 600 | 4 | 7 | — |
| 655 | 7 | 9 | 3 |
| 685 | 4 | 8 | — |
| 715 | 3 | 8 | 3 |
| 745 | 4 | 8 | — |

Experimental matrix - number of specimens per pyrolysis temperature and weight percent of poly(dimethylsiloxane) polymer in cyclohexane.

Results

FIG. 1 shows mean fracture stresses for each polymer concentrations as a function of pyrolysis temperature. ANOVA and a 95% multiple range test were used to evaluate significant differences among conditions. Within the 5 weight percent group, the 655° C. specimens differed from all others except those pyrolyzed at 600° C. In addition there were significant differences between both the 685° and 715° C. specimens compared with the 745° C. specimen group. Within the 0 weight percent group, only the two lowest temperature sets differ from the two highest temperature sets. Within the 20 weight percent group there was no statistical difference, probably in part due to the rather small number of specimens. Between concentration groups at 655° C., the 5 weight percent set differs from the 0 and 20 weight percent sets. Overall, the low temperature specimen groups were significantly stronger than the high temperature sets and a maximum may exist when the pre-ceramic polymer was used at an intermediate temperature.

Figure 2:
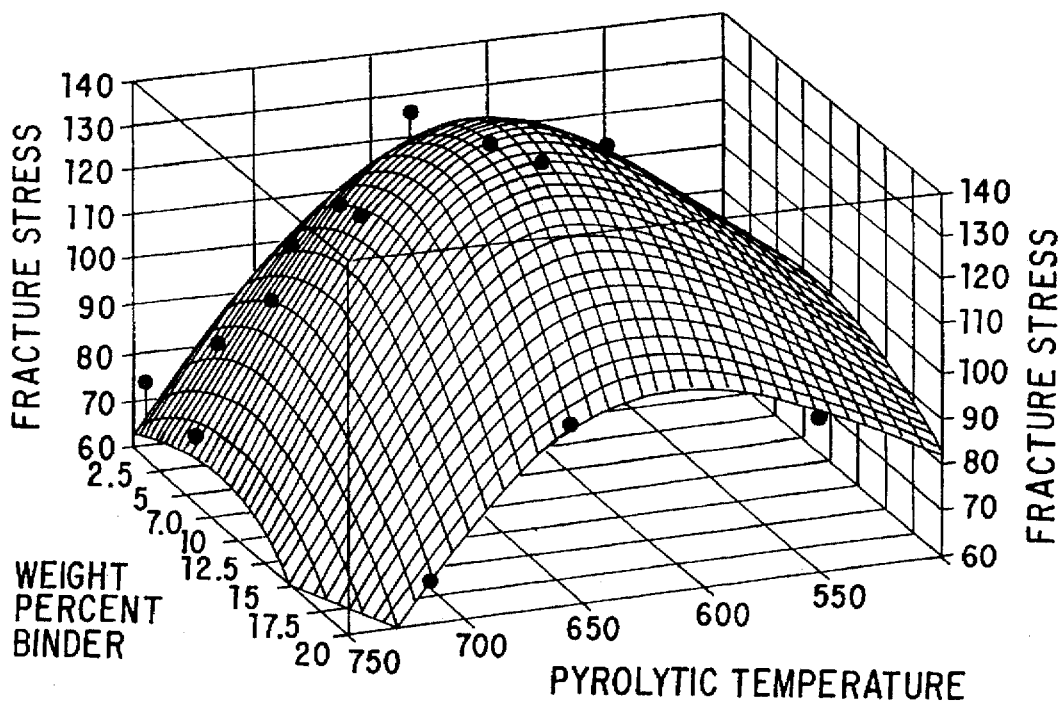
FIG. 2 is a graphic representation of the response surface fit to mean fracture stress data.

FIG. 2 is a three-dimensional response surface fit to the existing data set, having a degree of freedom adjusted $R^2$ equal to 0.85. Fracture stress, as the response variable, was plotted on the z axis versus pyrolysis temperature (y) and weight percent binder (x). This surface allows visualization of the behavior of a function representing some key aspects of the data. For example, the data suggests that a maximum strength response exists between 0 and 20 weight percent polymer and at a mid-pyrolsis temperature. The strength slope appears steeper towards higher temperatures than lower ones. Such response surface modeling can be used to make modifications of the disclosed embodiments.

Although we have emphasized the utility of the invention for manufacturing dental restorations, the invention is by no means limited to such utility but has general application to any instance where near net shape products are required. Thus, the invention may be used to make other prosthetic devices, as mentioned above for humans or animals.

The teachings of the invention may also be employed whenever low cost, low temperature ceramic composite materials are desired, such as substitutes for metal and other parts for aircraft, land, water or underwater vehicles, missiles, rockets, and other projectiles where near net shape is a requirement of the application.

Although we have disclosed methyl methacrylate as a preferable non-ceramic firing infiltrant, a large class of other monomers, oligomers and polymers are suitable as infiltrants, such as acrylics, styrenics and other vinyls, epoxies, urethanes, polyesters, polycarbonates, polyamides, radiopaque polymers and biomaterials. Specific examples include the following compounds: acenaphthylene, 3-aminopropyltrimethoxysilane, diglycidyletherbisphenol, 3-glycidylpropyltrimethoxysilane, tetrabromobisphenol-A-dimethacrylate, polyactide, polyglycolide, 1,6-hexamethylene dimethacrylate, 1,10-decamethylene dimethacrylate, benzyl methacrylate, butanediol monoacrylate, 1,3-butanediol diacrylate (1,3-butylene glycol diacrylate), 1,3-butylene glycol dimethacrylate), 1,4-butanediol diacrylate, 1,4-butanediol dimethacrylate, n-butyl acrylate, n-butyl methacrylate, t-butyl acrylate, t-butyl methacrylate, n-butyl vinyl ether, t-butylaminoethyl methacrylate, 1,3-butylene glycol diacrylate, cyclohexyl acrylate, cyclohexyl methacrylate, n-decyl acrylate, n-decyl methacrylate, diethylene glycol diacrylate, diethylene glycol dimethacrylate, dipentaerythritol monohydroxypentaacrylate, 2-ethyoxyethoxyethyl acrylate, 2-ethoxyethyl methacrylate, ethoxylated bisphenol A diacrylate, ethoxylated bisphenol A dimethacrylate, ethoxylated trimethylolpropane triacrylate, ethyl methacrylate, ethylene glycol dimethacrylate, 2-ethylhexyl acrylate, 2-ethylhexyl methacrylate, furfuryl methacrylate, glyceryl propoxy triacrylate, 1,6 hexanediol diacrylate, 1,6 hexanediol dimethacrylate, n-hexyl acrylate, n-hexyl methacrylate, 4-hydroxybutyl acrylate, (butanediol monoacrylate), 2-hydroxyethyl acrylate, hydroxyethyl methacrylate, hydroxypropyl acrylate, hydroxypropyl methacrylate, isobornyl acrylate, isobornyl methacrylate, isobutyl acrylate, isobutyl methacrylate, isobutyl vinyl ether, isodecyl acrylate, isodecyl methacrylate, isooctyl acrylate, isopropyl methacrylate, lauryl acrylate, lauryl methacrylate, maleic anhydride, methacrylic anhydride, 2-methoxyethyl acrylate, methyl methacrylate, neopentyl acrylate, neopentyl methacrylate, neopentyl glycol diacrylate, neopentyl glycol dimethacrylate, n-octadecyl acrylate, (stearyl acrylate), n-octadecyl methacrylate, (stearyl methacrylate), n-octyl acrylate, pentaerythritol tetraacrylate, pentaerythritol triacrylate, 2-phenoxyethyl acrylate, 2-phenoxyethyl methacrylate, 2-phenylethyl methacrylate, phenyl methacrylate, polybutadiene diacrylate oligomer, polyethylene glycol 200 diacrylate, polyethylene glycol 400 diacrylate, polyethylene glycol 200 dimethacrylate, polyethylene glycol 400 dimethacrylate, polyethylene glycol 600 dimethacrylate, polypropylene glycol monomethacrylate, propoxylated neopentyl glycol diacrylate, stearyl acrylate, stearyl methacrylate, 2-sulfoethyl methacrylate, tetraethylene glycol diacrylate, tetraethylene glycol dimethacrylate, tetrahydrofurfuryl acrylate, tetrahydrofurfuryl methacrylate, n-tridecyl methacrylate, triethylene glycol diacrylate, triethylene glycol dimethacrylate, trimethylolpropane triacrylate, trimethylolpropane trimethacrylate, 3-methacryloxypropyltrimethoxysilane, trimethylsilylmethacrylate, (trimethylsilymethyl) methacrylate, tripropylene glycol diacrylate, tris(2-hydroxyethyl)isoyanurate triacrylate, vinyl acetate, vinyl caprolactam, n-vinyl-2-pyrrolidone, zinc diacrylate and zinc dimethacrylate.

Another embodiment of the present invention substitutes a prepolymer or oligomer for some of the monomer used. The oligomers used are miscible with the monomers mentioned above. Preferably the oligomers are formed from one or more of the same monomers employed in the monomer system.

Additives to the pre-ceramic inorganic or organic precursors can include lithium, potassium, calcium, aluminum, alkali or alkaline earth cations, or other cations.

Example 3

The procedure of Example 2 was repeated except that a calcium phosphate hydroxyapatite obtained from Rhône-Poulenc Basic Chemicals in Shelton, Conn. was used as the ceramic powder to produce a sintered ceramic framework according to the invention.

Example 4

The procedure of Example 3 was repeated except that the calcium phosphate hydroxyapatite was prepared at the National Institute of Standards and Technology (NIST) in Gaithersburg, Md. according to the protocol for Standard Reference Material #2910 which was mixed with about 20 wt % poly(dimethylsiloxane) in a cyclohexane solvent and coated onto a titanium substrate. Upon firing at about 655° C. for about 10 minutes, the ceramic coating was bonded to the substrate.

Furthermore, it is to be understood that the crystalline form of the ceramic in the necks can be varied by post treatment of the partially sintered ceramic framework, i.e., an amorphous glass can be crystallized.

Having now disclosed our invention, it is readily apparent to those skilled in the art that modifications and variations may be made without departing from the spirit or scope of the appended claims.

We claim:

1. A process for low temperature formation of porous ceramic-based composite materials comprising the following steps:
   (a) mixing a ceramic powder with an organometallic pre-ceramic precursor;
   (b) heating, at a temperature from about 500° C. to about 1000° C., the mixture of step (a) to form a porous body of ceramic powder bonded by necks of ceramic material formed by heat decomposition of the pre-ceramic precursor.

2. The process of claim 1 wherein the organometallic pre-ceramic precursor is selected from the group consisting of polyorganozirconates, polyorganoaluminates, polysiloxanes, polysilanes, polysilazanes, polyphosphazenes, polyorganotitanates and mixtures thereof.

3. The process of claim 1 wherein the porous body is infiltrated with a material selected from the group consisting of monomers, oligomers, polymers, and mixtures thereof, which material is cured in situ.

4. The process of claim 1 wherein the pre-ceramic precursor is a poly(dimethylsiloxane).

5. The process of claim 1 wherein the heating is in air.

6. The process of claim 3 further comprising silanizing the porous body before the infiltrating step.

7. The process of claim 1 further comprising contacting the porous body with 3-methacryloxy-propyltrimethoxy silane before the infiltrating step.

8. The process of claim 4 wherein the heating is conducted at about 655° C. for about 10 minutes in air.

9. The process of claim 3 wherein the monomer is methyl methacrylate which is initiated by a process selected from the group consisting of thermally, chemically, photo- and combinations thereof.

10. The process of claim 3 wherein the curing is carried out at ambient temperature.

11. The process of claim 10 further comprising annealing the cured polymer at an elevated temperature.

12. The process of claim 10 further comprising post-curing the cured polymer at about 65° C.

13. The product produced by the process of claim 1.

14. The process of claim 1 wherein the mixture of step (a) is coated on a substrate prior to step (b).

15. The product formed by the process of claim 14.

16. The process of claim 14 wherein the porous body is infiltrated with a material selected from the group consisting of monomers, oligomers, polymers, and mixtures thereof, which material is cured in situ.

17. A composite material comprising a skeleton of ceramic particles bound together by ceramic bonds formed by decomposition of an inorganic or organic material, said ceramic particles being selected from the group consisting of alumina, calcium hydroxyapatites, feldspathic ceramic, titanium dioxide, zirconia, biologically active glasses and spinels, said skeleton containing an interpenetrating phase of a cured organic resin.

18. The product of claim 17 wherein the organic resin is formed by polymerizing a monomer or oligomer selected from the group consisting of monomers and oligomers having acrylate or methacrylate moieties.

19. A dental restoration produced by the process of claim 3.

20. A prosthesis or cosmetic product for humans or animals produced by the process of claim 1.

21. A near net shape composite material comprising a sintered ceramic skeleton which contains an interpenetrating phase of cured organic resin, said near net shape composite material possessing a mean tensile strength of at least 50 MPa.

22. The process of claim 2 wherein the pre-ceramic precursor further contains additives.

23. The process of claim 22 wherein the additives are cations selected from the group consisting of lithium, potassium, calcium, aluminum, and mixtures thereof.

24. The process of claim 1 wherein the heating is in nitrogen.

25. A dental restoration produced by the process of claim 14.

26. The process of claim 2 where the pre-ceramic precursor is selected from the group consisting of polycarbosilanes, polyborosilanes, and mixtures thereof.

27. The process of claim 22 wherein the additives are cations selected for the group consisting of alkali or alkaline earth metals and mixtures thereof.

* * * * *